(12) United States Patent
Clayton et al.

(10) Patent No.: US 9,795,289 B2
(45) Date of Patent: Oct. 24, 2017

(54) LIGHT FOR ORAL ANESTHESIA INJECTION SYRINGE

(71) Applicants: M. Wade Clayton, Germantown, TN (US); Jimmy E. Brown, Bartlett, TN (US)

(72) Inventors: M. Wade Clayton, Germantown, TN (US); Jimmy E. Brown, Bartlett, TN (US)

(*) Notice: Subject to any disclaimer, the term of this patent is extended or adjusted under 35 U.S.C. 154(b) by 0 days.

(21) Appl. No.: 15/007,142

(22) Filed: Jan. 26, 2016

(65) Prior Publication Data

US 2016/0213240 A1    Jul. 28, 2016

Related U.S. Application Data

(60) Division of application No. 14/165,537, filed on Jan. 27, 2014, now Pat. No. 9,241,618, which is a
(Continued)

(51) Int. Cl.
*A61B 1/247* (2006.01)
*A61B 1/06* (2006.01)
(Continued)

(52) U.S. Cl.
CPC ............ *A61B 1/247* (2013.01); *A61B 1/06* (2013.01); *A61B 1/0607* (2013.01); *A61B 1/24* (2013.01);
(Continued)

(58) Field of Classification Search
CPC .. A61B 1/24; A61B 1/247; A61B 1/06; A61B 1/0607; A61B 19/08; A61M 5/178;
(Continued)

(56) References Cited

U.S. PATENT DOCUMENTS

| 2,437,697 A | 3/1948 | Kalom |
| 4,040,419 A | 8/1977 | Goldman |

(Continued)

FOREIGN PATENT DOCUMENTS

| DE | 3322923 A1 | 1/1985 |
| DE | 10 2006 018 143 A1 | 10/2007 |

(Continued)

OTHER PUBLICATIONS

International Searching Authority of US PCT Receiving Office, Notification of Transmittal of the International Search Report and the Written Opinion of the International Searching Authority or Declaration, Form PCT/ISA/220 for International Application PCT/US2014/013251 (dated May 12, 2014; published Jul. 31, 2014) World Intellectual Property Organization, Geneva, Switzerland.

(Continued)

*Primary Examiner* — Theodore Stigell
(74) *Attorney, Agent, or Firm* — Walker, McKenzie & Walker, P.C.

(57) ABSTRACT

A light for use with an oral anesthesia syringe that is received into a passageway of a barrel of the light. When the syringe is received into a first opening in a proximal end of the barrel's passageway, the needle of the syringe extends through a second opening at the proximal end of the barrel. At least one lamp and preferably a plurality of lamps at the distal end of the barrel illuminate the needle and the interior of a patient's mouth. A battery is included in the light for powering the lamps. The insertion of the syringe into the barrel may a pair of contacts to cause the battery to power the lamps, or the battery may be removed to remove power from the lamps. A disposable integrated syringe and light combination is also described.

2 Claims, 5 Drawing Sheets

Related U.S. Application Data continuation-in-part of application No. 13/750,111, filed on Jan. 25, 2013, now Pat. No. 8,911,409.

(51) Int. Cl.

| A61C 19/08 | (2006.01) |
|---|---|
| A61M 5/24 | (2006.01) |
| A61B 1/24 | (2006.01) |
| A61M 5/178 | (2006.01) |
| A61M 5/31 | (2006.01) |

(52) U.S. Cl.
CPC ............ *A61C 19/08* (2013.01); *A61M 5/178* (2013.01); *A61M 5/24* (2013.01); *A61M 5/3134* (2013.01); *A61M 2005/2407* (2013.01); *A61M 2205/587* (2013.01); *A61M 2205/8206* (2013.01)

(58) Field of Classification Search
CPC .............. A61M 5/24; A61M 5/3134; A61M 2205/587; A61M 2205/8206; A61M 2005/2407; A61C 19/08
See application file for complete search history.

(56) References Cited

U.S. PATENT DOCUMENTS

| | | | |
|---|---|---|---|
| 5,415,543 | A | 5/1995 | Rozmajzl, Jr. |
| 5,899,692 | A | 5/1999 | Davis et al. |
| 6,159,161 | A | 12/2000 | Hodosh |
| 6,595,962 | B1 | 7/2003 | Perthu |
| 6,988,814 | B1 | 1/2006 | Correa |
| 7,351,231 | B2 | 4/2008 | Young |
| 7,896,838 | B2 | 3/2011 | Devega |
| 8,170,657 | B1 | 5/2012 | Ehrenreich |
| 8,371,848 | B2 | 2/2013 | Okawa et al. |
| 8,613,618 | B2 | 12/2013 | Brokx |
| 2005/0063177 | A1 | 3/2005 | Correa |
| 2005/0070848 | A1 | 3/2005 | Kim et al. |
| 2005/0080384 | A1* | 4/2005 | Green ............ A61M 5/31511 604/218 |
| 2005/0084816 | A1 | 4/2005 | Mehdizadeh |
| 2006/0019220 | A1 | 1/2006 | Loebel |
| 2008/0234625 | A1 | 9/2008 | Dacquay et al. |
| 2009/0093692 | A1 | 4/2009 | Hansma |
| 2009/0216193 | A1 | 8/2009 | Schriver et al. |
| 2010/0069851 | A1 | 3/2010 | Vad et al. |
| 2010/0081919 | A1 | 4/2010 | Hyde et al. |
| 2010/0286659 | A1 | 11/2010 | Terrill et al. |
| 2011/0033817 | A1 | 2/2011 | Mckay |
| 2011/0143305 | A1 | 6/2011 | Wagner et al. |
| 2011/0190693 | A1 | 8/2011 | Takatsuka |
| 2011/0196312 | A1 | 8/2011 | Devega |
| 2013/0203014 | A1 | 8/2013 | Lieb et al. |

FOREIGN PATENT DOCUMENTS

| | | | |
|---|---|---|---|
| DE | 102006018143 | * | 10/2007 |
| DE | 102006018143 A1 | | 10/2007 |
| EP | 0 238 778 A2 | | 9/1987 |
| EP | 0 238 778 A3 | | 9/1987 |
| EP | 238778 A2 | | 9/1987 |
| JP | 2001137341 A | | 5/2001 |

OTHER PUBLICATIONS

International Searching Authority of US PCT Receiving Office, International Search Report, Form PCT/ISA/210 for International Application PCT/US2014/013251 (dated May 12, 2014; published Jul. 31, 2014) World Intellectual Property Organization, Geneva, Switzerland.

International Searching Authority of US PCT Receiving Office, Search History for International Search Report for International Application PCT/US2014/013251 (dated May 12, 2014; published Jul. 31, 2014) World Intellectual Property Organization, Geneva, Switzerland.

International Searching Authority of US PCT Receiving Office, Written Opinion of the International Searching Authority, Form PCT/ISA/237 for International Application PCT/US2014/013251 (dated May 12, 2014; published Jul. 31, 2014) World Intellectual Property Organization, Geneva, Switzerland.

International Searching Authority of US PCT Receiving Office, Notification of Transmittal of the International Search Report and the Written Opinion of the International Searching Authority or Declaration, Form PCT/ISA/220 for International Application PCT/US2014/048318 (dated Jan. 16, 2015; published Jul. 30, 2015) World Intellectual Property Organization, Geneva, Switzerland.

International Searching Authority of US PCT Receiving Office, International Search Report, Form PCT/ISA/210 for International Application PCT/US2014/048318 (dated Jan. 16, 2015; published Jul. 30, 2015) World Intellectual Property Organization, Geneva, Switzerland.

International Searching Authority of US PCT Receiving Office, Search History for International Search Report for International Application PCT/US2014/048318 (dated Jan. 16, 2015; published Jul. 30, 2015) World Intellectual Property Organization, Geneva, Switzerland.

International Searching Authority of US PCT Receiving Office, Written Opinion of the International Searching Authority, Form PCT/ISA/237 for International Application PCT/US2014/048318 (dated Jan. 16, 2015; published Jul. 30, 2015) World Intellectual Property Organization, Geneva, Switzerland.

Semiconductor Components Industries, LLC, ESD9B, SZESD9B—Transient Voltage Suppressors (Feb. 14, 2014) Semiconductor Components Industries, LLC, Denver, Colorado, USA.

Microchip Technology Inc., MCP65R41/6—3 µA Comparator with Integrated Reference Voltage (Sep. 2011) Microchip Technology Inc., Chandler, Arizona, U.S.A.

European Patent Office, Communication Pursuant to Rule 164(1) EPC, Partial Supplementary Search Report for Application EP 14 74 3696.8 (EPO national stage of PCT/US2014/013251) (Aug. 31, 2016), European Patent Office, Munich, Germany (11 pages).

\* cited by examiner

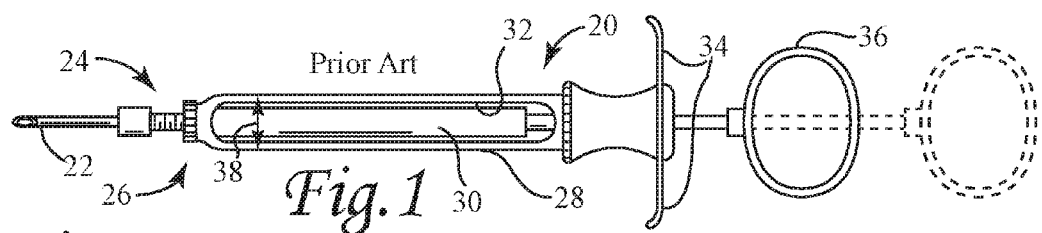
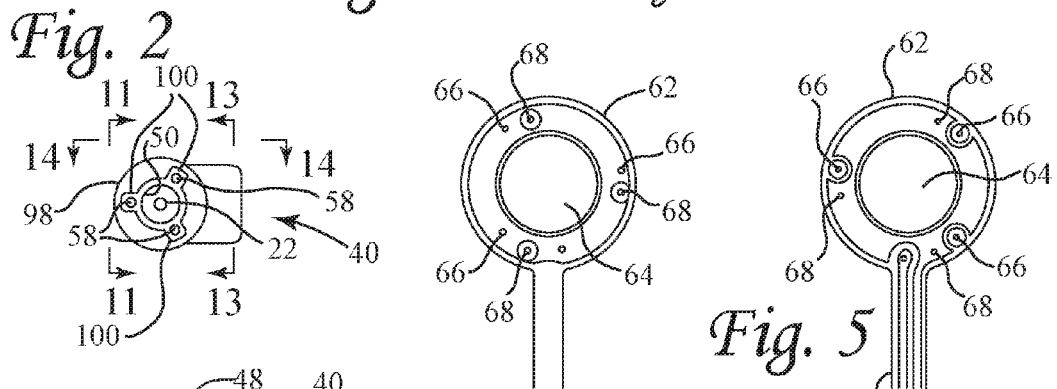
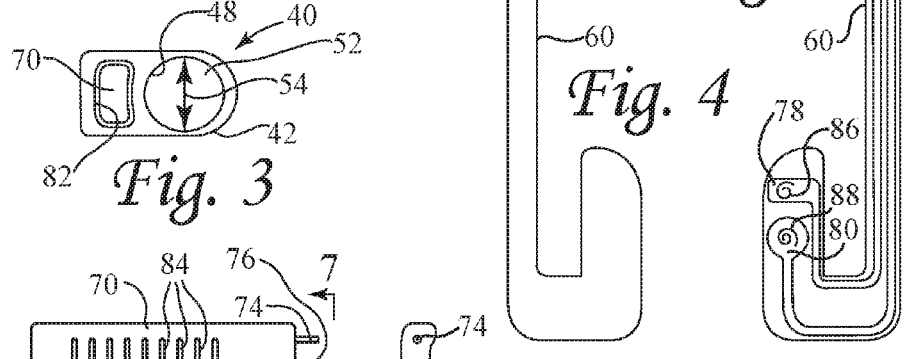
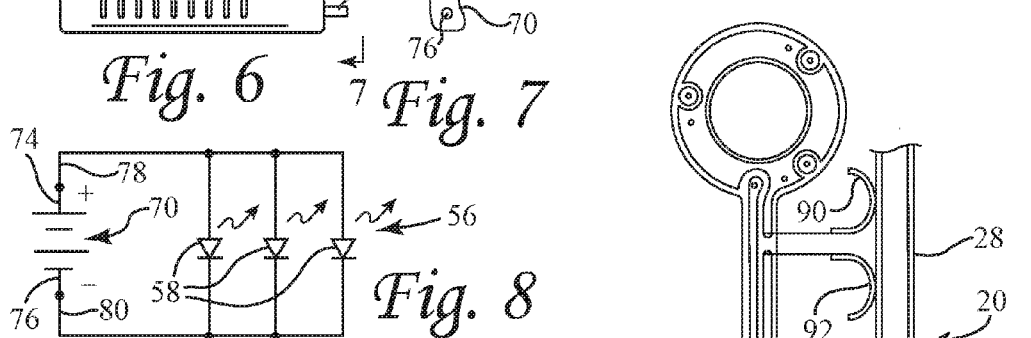
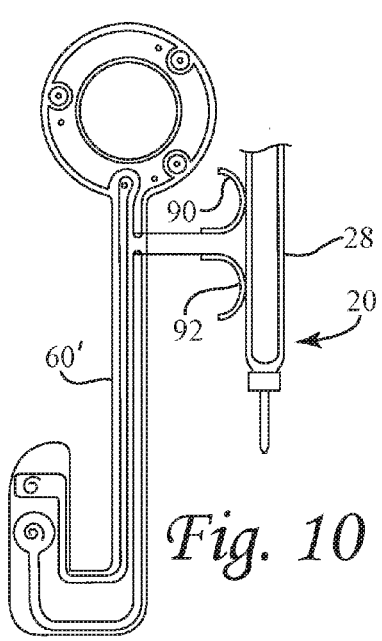
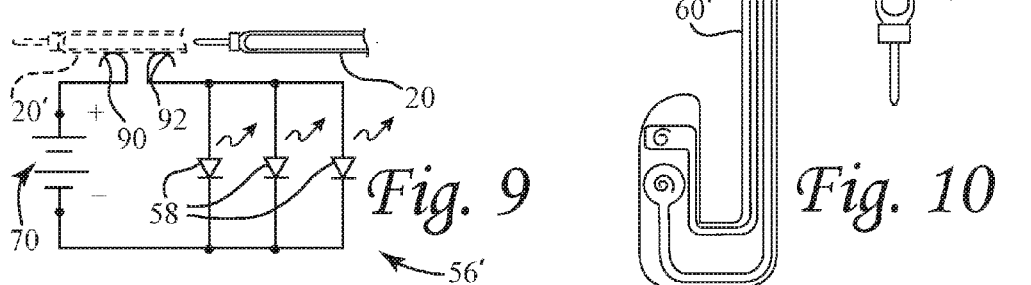

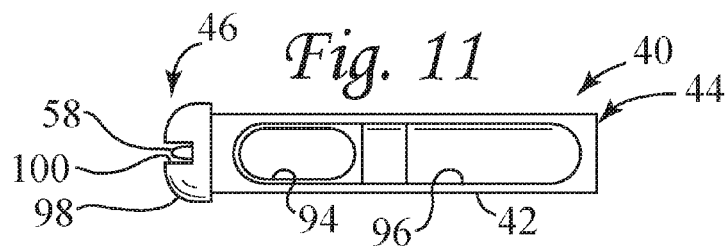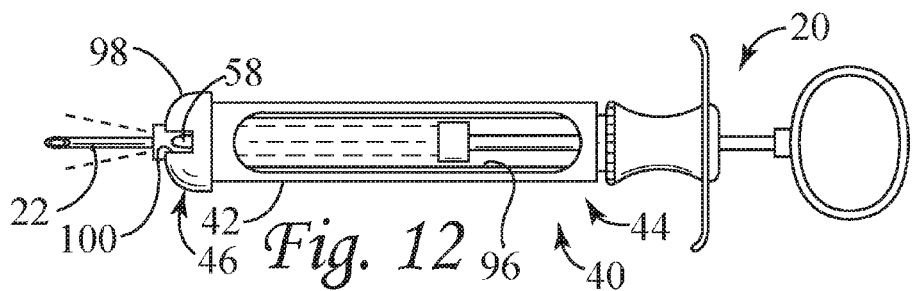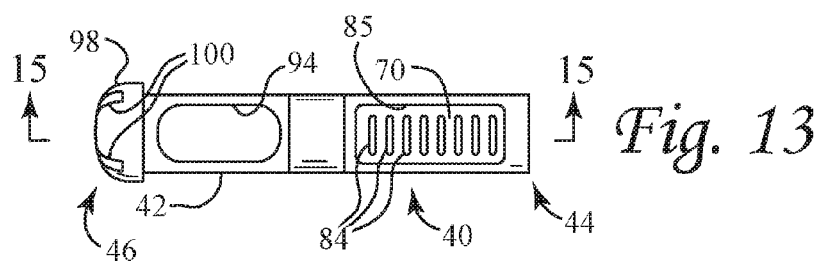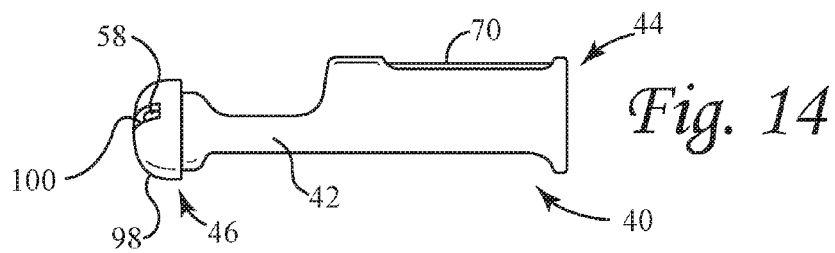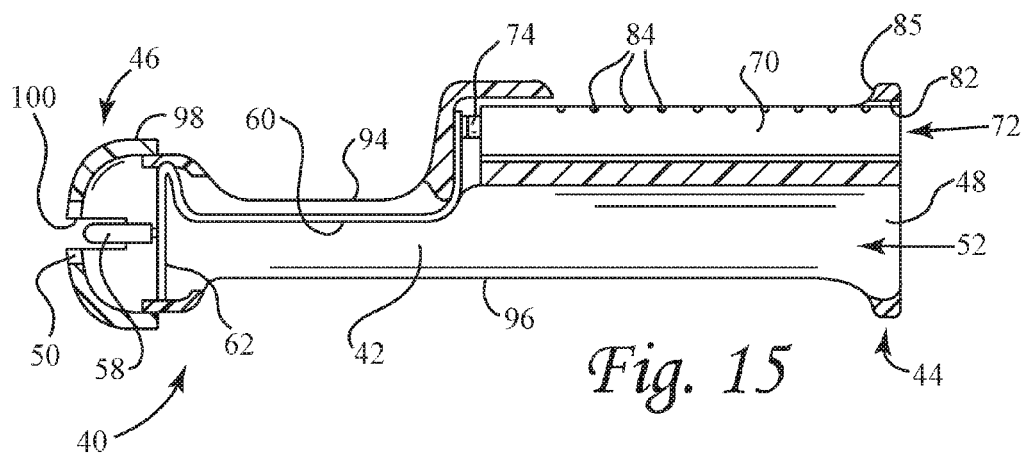

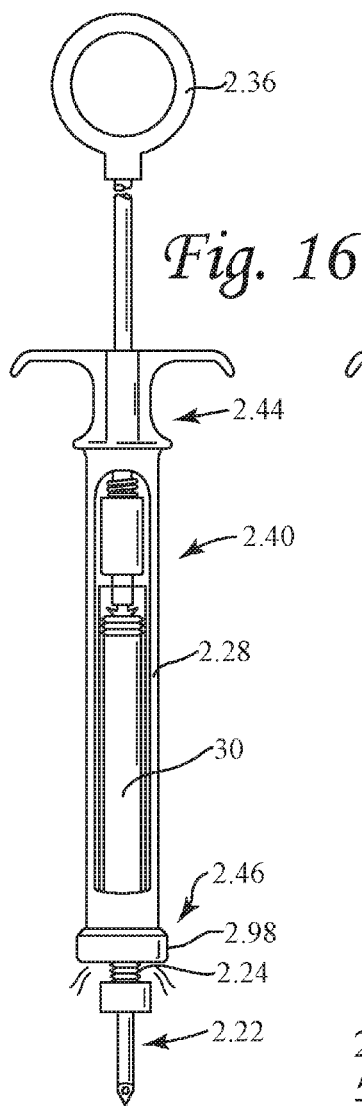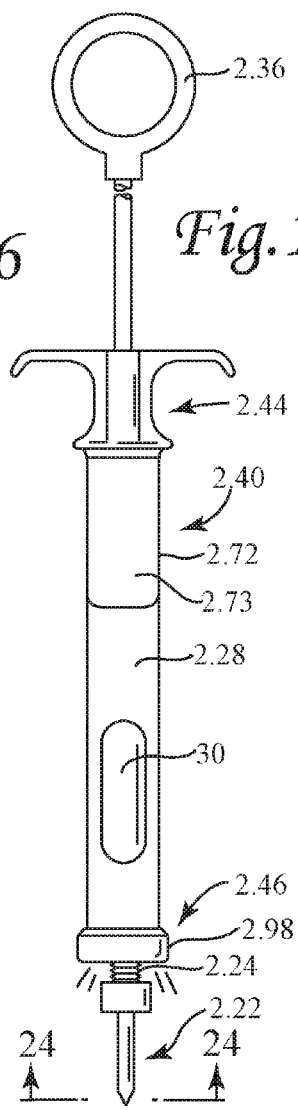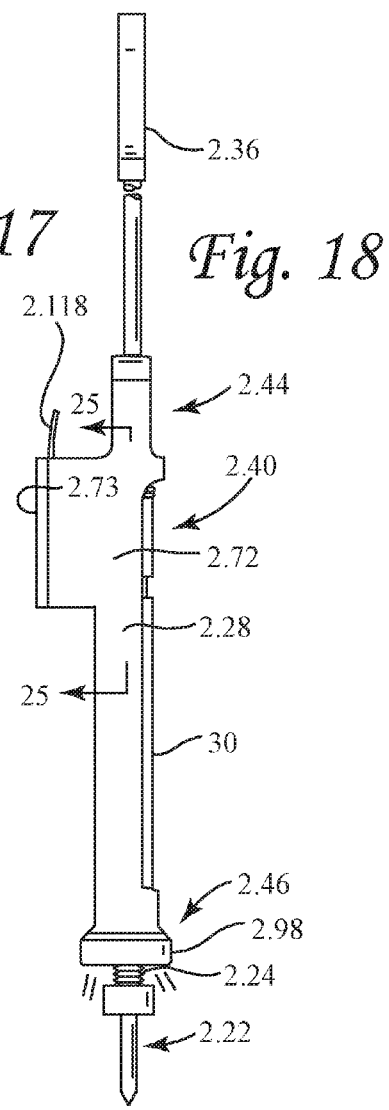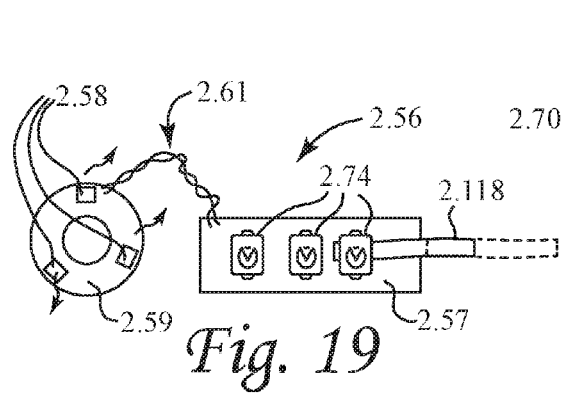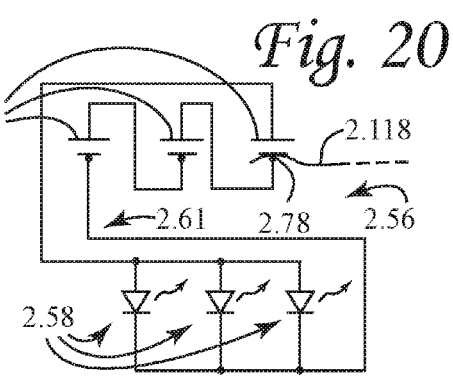

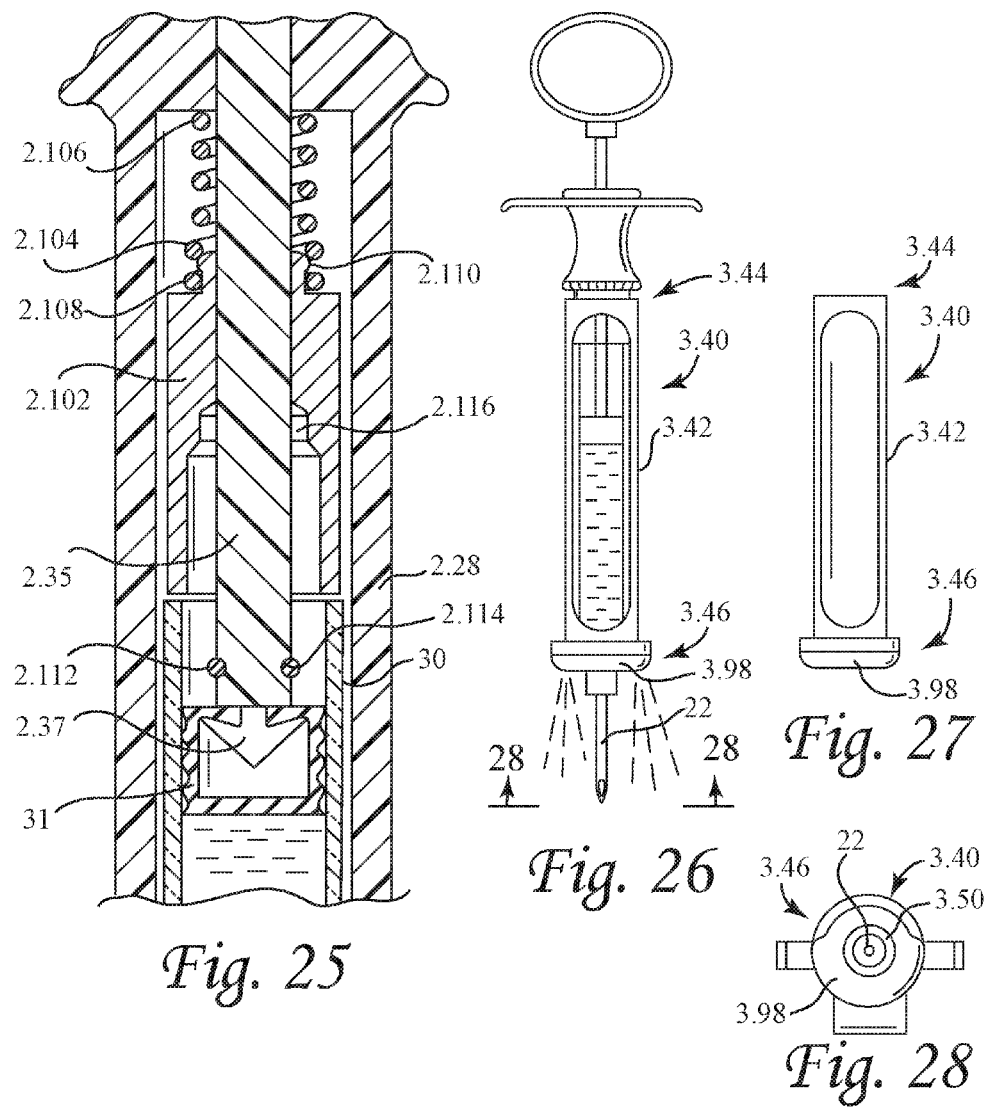

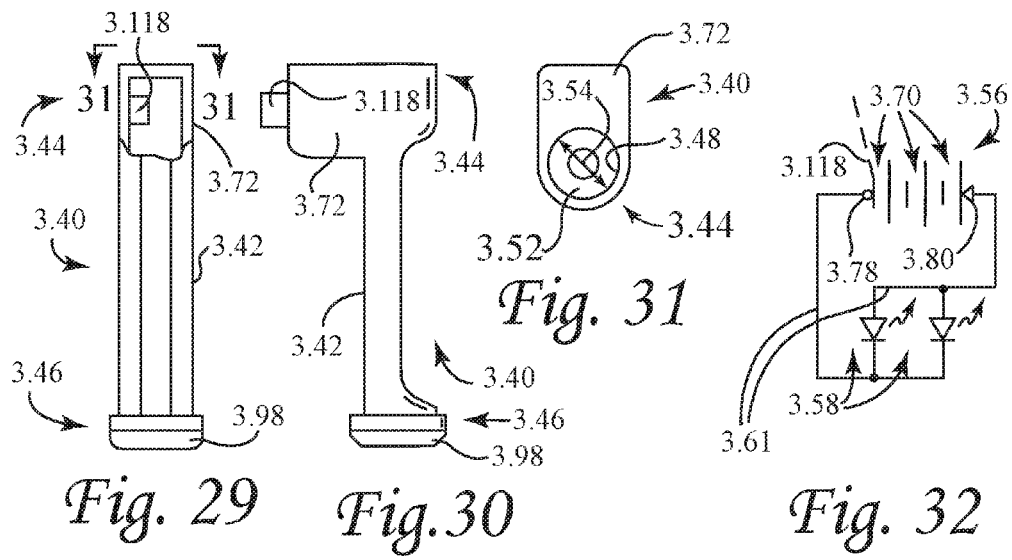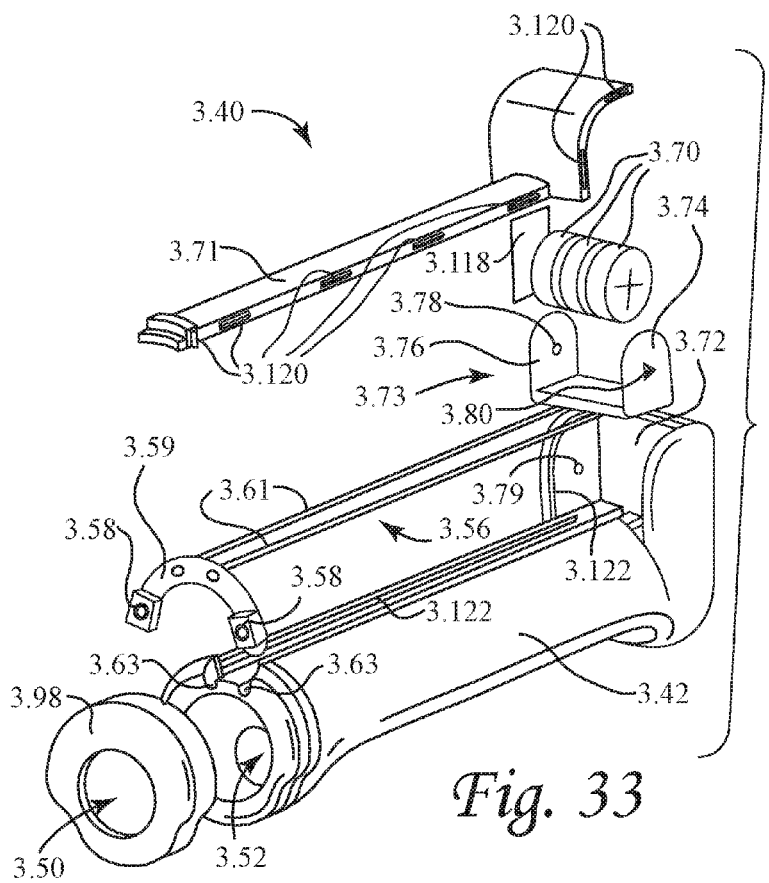

LIGHT FOR ORAL ANESTHESIA INJECTION SYRINGE

CROSS REFERENCE TO RELATED APPLICATIONS

This application is a division of U.S. application Ser. No. 14/165,537, filed Jan. 27, 2014, and due to issue on Jan. 26, 2016, as U.S. Pat. No. 9,241,618, fully included by reference herein, and claims priority benefit thereof. application Ser. No. 14/165,537, in turn, was a continuation-in-part of U.S. patent application Ser. No. 13/750,111, filed Jan. 25, 2013, which issued on Dec. 16, 2014, as U.S. Pat. No. 8,911,409, entitled "Light for Oral Anesthesia Injection Syringe", fully included by reference herein, and claims priority benefit thereof.

STATEMENT REGARDING FEDERALLY SPONSORED RESEARCH OR DEVELOPMENT

Not applicable.

REFERENCE TO COMPACT DISC(S)

Not applicable.

BACKGROUND OF THE INVENTION

1. Field of the Invention

The present invention relates, in general, to the administration of oral anesthesia into a patient's mouth using a syringe, and, in particular, to lighting of the interior of a patient's mouth during the administration of oral anesthesia.

2. Information Disclosure Statement

It is well-known for dentists to use prior art oral anesthesia injection syringes, such as the prior art syringe shown in FIG. 1, to anesthetize a patient's mouth during dental surgery. A problem is that access to the inside of a patient's mouth is limited by the size of the patient's mouth opening, and it is difficult to adequately illuminate the inside of the patient's mouth so that the dentist can view the injection site during application of the anesthesia. Typically a light mounted on a movable arm is used to illuminate the inside of the patient's mouth, but the dentist's head and hands can impede illumination of the inside of the patient's mouth by the light. Also, when the dentist moves to various injection sites inside the patient's mouth, the light on the movable arm may have to be repositioned between injections so as to provide sufficient illumination inside the patient's mouth.

It is therefore desirable to have a light inside the patient's mouth that directly illuminates the desired injection sites as the oral anesthesia injection syringe is moved from one injection site to another. It is further desirable to provide a "hands free" means of lighting the inside of the patient's mouth that moves with the oral anesthesia injection syringe and that does not require an additional hand to manage the positioning of the lighting of the inside of the patient's mouth.

It is further desirable to provide a single-use disposable oral anesthesia injection syringe that illuminates the inside of a patient's mouth.

BRIEF SUMMARY OF THE INVENTION

The present invention is a light for use with an oral anesthesia syringe that is received into a passageway of a barrel of the light. When the syringe is received into a first opening in a proximal end of the barrel's passageway, the needle of the syringe extends through a second opening at the proximal end of the barrel. At least one lamp and preferably a plurality of lamps at the distal end of the barrel illuminate the needle and the interior of a patient's mouth. A battery is provided in the light for powering the lamps. The insertion of the syringe into the barrel closes a pair of contacts to cause the battery to power the lamps, or the battery may be removed in order to remove power from the lamps.

It is an object of the present invention to provide illumination of the needle of an oral anesthesia syringe and of the anesthesia injection site within a patient's mouth. It is a further object of the invention to provide self-contained "hands free" illumination within the patient's mouth that moves together with the anesthesia syringe, without having cords or wires that extend out of the patient's mouth to an external power source.

It is a further object of the present invention to provide a single-use disposable oral anesthesia injection syringe that illuminates the inside of a patient's mouth.

BRIEF DESCRIPTION OF THE SEVERAL VIEWS OF THE DRAWING

FIG. 1 is a side view of a prior art oral anesthesia injection syringe for use with the present invention.

FIG. 2 is a front view of the distal end of the present invention.

FIG. 3 rear view of the proximal end of the present invention with the battery inserted.

FIG. 4 is a plan view of a first side of the first embodiment of the flexible circuitry of the present invention.

FIG. 5 is a plan view of a second side of the first embodiment of the flexible circuitry of the present invention.

FIG. 6 is a side view of the battery of the present invention, removed from the battery compartment.

FIG. 7 is an end view of the battery of the present invention showing the battery contacts, taken substantially along the line 7-7 shown in FIG. 6.

FIG. 8 is a schematic of the present invention using the first embodiment of the flexible circuitry.

FIG. 9 is a schematic of the present invention using the second embodiment of the flexible circuitry, showing the circuit being completed by the metal barrel of the oral anesthesia injection syringe.

FIG. 10 is a plan view of the second side of the second embodiment of the flexible circuitry of the present invention, showing the circuit being completed by the metal barrel of the oral anesthesia injection syringe.

FIG. 11 is a bottom view of the present invention, taken substantially along the line 11-11 shown in FIG. 2.

FIG. 12 is another bottom view of the present invention, similar to FIG. 11 but with the oral anesthesia injection syringe being inserted therewithin for use in combination with the present invention.

FIG. 13 is top view of the present invention, taken substantially along the line 13-13 shown in FIG. 2.

FIG. 14 is side view of the present invention, taken substantially along the line 14-14 shown in FIG. 2. The view from the other side is substantially a mirror image of FIG. 14.

FIG. 15 is a side sectional view of the present invention showing the internal structure, taken substantially along the line 15-15 shown in FIG. 13.

FIG. 16 shows a bottom view of a second preferred embodiment of the oral injection syringe of the present invention that is disposable and single-use.

FIG. 17 shows a top view of the second preferred embodiment of the oral injection syringe of the present invention.

FIG. 18 shows a side view of the second preferred embodiment of the oral injection syringe of the present invention, taken substantially along the line 18-18 shown in FIG. 17. The view from the other side is substantially a mirror image of FIG. 18.

FIG. 19 shows the power circuit board with batteries of the second preferred embodiment of the oral injection syringe of the present invention connected by wires to its LED assembly circuit board, and showing in dotted outline the removal of the insulating strip to apply power to the LED lights.

FIG. 20 shows a schematic of the second preferred embodiment of the oral injection syringe of the present invention and showing in dotted outline the removal of the insulating strip to apply power to the LED lights.

FIG. 21 is a side view of the cylindrically-symmetric sleeve of the second preferred embodiment of the oral injection syringe of the present invention. The view from all sides is the same.

FIG. 22 is a rear view of the cylindrically-symmetric sleeve, taken substantially along the line 22-22 shown in FIG. 21.

FIG. 23 is a front view of the cylindrically-symmetric sleeve, taken substantially along the line 23-23 shown in FIG. 21.

FIG. 24 is a front view of the second preferred embodiment of the oral injection syringe of the present invention, taken substantially along the line 24-24 shown in FIG. 17.

FIG. 25 is a partial sectional view of the second preferred embodiment of the oral injection syringe of the present invention, showing details of the cylindrically-symmetric sleeve, spring, and barbed shaft of the plunger, taken substantially along the line 25-25 shown in FIG. 18.

FIG. 26 is a bottom view of the third embodiment of the light of the present invention with the oral anesthesia injection syringe being inserted therewithin for use in combination with the third embodiment.

FIG. 27 is another bottom view of the third embodiment of the light of the present invention, similar to FIG. 26 but without the oral anesthesia injection syringe being inserted.

FIG. 28 is a front view of the third embodiment of the light of the present invention, taken substantially along the line 28-28 shown in FIG. 26.

FIG. 29 is a top view of the third preferred embodiment of the light of the present invention without the oral anesthesia injection syringe being inserted.

FIG. 30 is a side view of the third preferred embodiment of the light of the present invention without the oral anesthesia injection syringe being inserted. The view from the other side is substantially a mirror image of FIG. 30.

FIG. 31 is a rear view of the third preferred embodiment of the light of the present invention without the oral anesthesia injection syringe being inserted, taken substantially along the line 31-31 shown in FIG. 29.

FIG. 32 is a schematic of the third preferred embodiment of the light of the present invention, showing in dotted outline the removal of the insulating strip to apply power to the LED lights.

FIG. 33 is an exploded perspective view of the third preferred embodiment of the light of the present invention, showing how the various pieces are assembled together.

DETAILED DESCRIPTION OF THE INVENTION

FIG. 1 shows a typical well-known prior art oral anesthesia syringe 20 such as would be used with the present invention. A suitable oral anesthesia injection syringe for use with the present invention is the well-known oral anesthesia injection syringe sold by Patterson Dental Supply, Inc., 1031 Mendota Heights Rd., St. Paul, Minn. 55120, U.S.A. The syringe 20 typically has a hypodermic needle 22 that is threadedly received onto a fitting 24 at the front or distal end 26 of the tubular body 28 of the syringe 20. A glass vial 30 of a local anesthetic is received into the body 28, and elongated side openings 32 are provided in the body 28 so that the amount of anesthetic within vial 30 can be observed. Finger grips 34 are provided for the dentist's fingers, and a thumb-operated plunger 36 is pushed into the vial 30 to cause injection of the anesthetic through the hypodermic needle 22, with an outer position of plunger 36 being shown in dotted outline. The parts of syringe 20 are typically made of stainless steel so that the syringe 20 may be sterilized in an autoclave. The tubular body 28 of the syringe 20 has a certain body outer diameter 38, typically about 10 mm.

FIGS. 2-15 of the drawings show the structure of the light 40 of the first preferred embodiment of the present invention, with FIGS. 9 and 10 showing an alternate embodiment, described hereinbelow, of the circuitry.

Light 40 includes a barrel 42 having a proximal end 44 and a distal end 46, and barrel 42 has a first opening 48 at proximal end 44 and a second opening 50 at distal end 46. Barrel 42 further has a longitudinal passageway 52 therethrough from first opening 48 to second opening 50, with passageway 52 having a transverse inner diameter 54 larger than the certain body outer diameter 38, for closely receiving the tubular body 28 of syringe 20 therewithin, with the tubular body 28 of syringe 20 extending through the first opening 48 and with the needle 22 extending out of the second opening 50 as best seen in FIG. 12. Preferably the transverse inner diameter 54 is about 1 mm or so larger than the certain body outer diameter 38 so that the syringe 20 will be frictionally retained within the passageway 52 of light 40. It will be understood that first opening 48, second opening 50, and passageway 52 are preferably co-axial on the longitudinal axis of barrel 42.

Light 40 further includes an electrical circuit 56 including at least one lamp 58 and preferably a plurality of lamps 58, such as the three light emitting diode ("LED") lamps shown in the preferred embodiments of light 40, proximate the distal end 46 of barrel 42, preferably encircling second opening 50 so as to fully illuminate the needle 22 and the anesthesia injection site in the patient's mouth. Electrical circuit 56 preferably includes a printed circuit pattern on a piece of flexible mylar 60 having a ring 62 with a center hole 64 to allow the needle of the syringe 22 to pass therethrough. Each lamp 58 is respectively mounted within a pair of holes 66, 68 in ring 62 that complete the circuit to a battery 70. Battery 70 is preferably rechargeable, as by putting battery 70 in a well-known battery charger, and is received in a battery compartment 72 of barrel 42. Battery 70 has a pair of contacts 74, 76 that contactingly and matingly engage contacts 78, 80 on the mylar circuitry. Battery 70 is preferably asymmetrically shaped to match the opening 82 of compartment 72 so that battery 70 can only be inserted correctly into compartment 72, and a plurality of small transverse channels 84 are preferably provided on an outer surface of battery 70 for ease of removal of the battery 70 as by engaging channels 84 with a user's fingernail through an access opening 85 into battery compartment 72. If desired, contacts 78, 80 on the mylar circuitry may be provided with springs 86, 88 to provide better contact with contacts 74, 76 of battery 70.

In the first embodiment 56 of the electrical circuit, power is applied to lamps 58 when the battery 70 is inserted into the battery compartment 72, thereby completing the circuit as battery contacts 74, 76 connectingly engage with contacts 78, 80 on the mylar circuitry. Likewise, power is removed from lamps 58 when the battery 70 is removed from the battery compartment 72.

An alternate or second embodiment 56' of the electrical circuit is shown in FIGS. 9 and 10, in which a modified version 60' of the mylar circuitry is used. It shall be understood that many aspects of the two preferred embodiments of the electrical circuits 60, 60' are substantially the same, and only the differences will be treated in detail, it being understood that similar structural features of the two embodiments perform similar functions.

In the second embodiment 56' of the electrical circuit, the electrical circuit 56' includes a pair of contacts 90, 92, preferably leaf spring contacts as shown, interposed between battery 70 and lamps 58. Contacts 90, 92 have a first condition, when the tubular body 28 of syringe 20 is not received within passageway 52, in which there is no electrical continuity between contacts 90, 92 (see solid outline of syringe 20 in FIG. 9), and a second condition, when the tubular body 28 of syringe 20 is received within passageway 52 (see dotted outline of syringe 20' in FIG. 9, and solid outline of syringe 20 in FIG. 10), in which there is caused to be electrical continuity between contacts 90, 92. Preferably this second condition of electrical continuity is made by the metal of tubular body 28 of syringe 20 completing the circuit between contacts 90, 92 and causing current to flow between contacts 90 and 92 through the conducting metal of tubular body 28, but the electrical continuity may be caused by mechanical engagement of tubular body 28 with one or both of contacts 90, 92 so as to cause contacts 90 and 92 to directly engage each other for current flow therebetween.

Preferably, the barrel 42 may include one or more elongated viewing openings 94, 96 so that the amount of anesthetic within vial 30 of syringe 20 can be observed during administration of local anesthesia to the patient. A cap 98 is preferably included at the distal end 46 of barrel 42 with there being a slot 100 in cap 98 in alignment with each lamp 58 to allow illumination from lamps 58 to pass to the anesthesia site and to the needle 22. Light 40 is preferably constructed of materials allowing disinfecting of the light before and after use.

To use the light of the first preferred embodiment of the present invention, the battery 70 is first charged in a well-known battery charger and then is inserted into the battery compartment 72. The hypodermic needle 22 is threadedly received onto fitting 24, and a vial 30 of anesthetic is placed within the syringe 20, and the syringe 20 is then inserted into and received within the passageway 52 of the light 40, with the tubular body 28 of the syringe 20 extending through the first opening 48 and with hypodermic needle 22 extending out of second opening 50. The lamps 58 will illuminate the needle 22 and the anesthesia injection site within the patient's mouth as the syringe 20 is used.

FIGS. 16-24 show a second preferred embodiment of an oral injection syringe 2.40 of the present invention, in which the syringe and the light are provided as an integrated unit. FIGS. 26-33 show a third preferred embodiment of the light 3.40 of the present invention. Like the first preferred embodiment 40 of the light of the present invention, the third embodiment light 3.40 of the present invention is used with a typical well-known prior art oral anesthesia syringe 20 as previously described in connection with the first embodiment light 40 and as shown in FIG. 1.

The construction of the second preferred embodiment 2.40 permits the syringe with light combination 2.40 to be provided pre-sterilized in a sealed sterile package that is opened when the syringe is needed to be used. Such a syringe and light combination 2.40 permits the syringe and light combination to be disposed after the single use, thereby reducing or eliminating the possibility of contamination from patient to patient of germs that are difficult if not impossible to kill by standard autoclave or chemical sterilization practices. While the syringe and light combination of the present invention could be sterilized by standard autoclave or chemical sterilization procedures, the inexpensive construction of the syringe and light combination of the present invention permits greater patient safety at minimal cost by having the syringe and light combination 2.40 be disposable and single use. Identifying reference designators for the second preferred embodiment 2.40 of the invention and the third preferred embodiment 3.40 of the present invention are marked similarly to the first embodiment, with the reference designators for the second preferred embodiment having a prefix of "2." and with the reference designators for the third preferred embodiment having a prefix of "3.", and with similar structural features of the first, second, and third embodiments having the same suffix (e.g., "40", "2.40", "3.40", etc.). It shall be understood that many aspects of the three preferred embodiments are substantially the same, and only the differences will be treated in detail, it being understood that similar structural features of the various embodiments perform similar functions.

Syringe with light combination 2.40 includes a body 2.28 having a proximal end 2.44 and a distal end 2.46, with distal end 2.46 being adapted, as by threaded fitting 2.24, for receipt of a hypodermic needle 2.22. As with all embodiments, the syringe body 2.28 receives therewithin a vial 30 of local anesthetic. Just as with prior art oral anesthesia syringes, embodiment 2.40 includes a thumb-operated plunger 2.36 that has a barb 2.37 that is engagingly pushed into the rubber plug 31 of anesthesia vial 30.

Syringe with light combination 2.40 also preferably includes a collet or cylindrically-symmetric sleeve 2.102 and compression spring 2.104 mounted upon the shaft 2.35 of plunger 2.36, as best seen in FIG. 25. Compression spring 2.104 preferably tapers from an outer diameter of about 8.8 mm at its proximal end 2.106 to an outer diameter of about 9.75 mm at its distal end 2.108, and distal end 2.108 engages with and is held by a nipple 2.110 of sleeve 2.102. Preferably one "dead" coil at the proximal end 2.106 of spring 2.104 and two "dead" coils at the distal end 2.108 of spring 2.104, and spring 2.104 preferably has a compression force of about 70 g/mm. The purpose of spring 2.104 and sleeve 2.102 is to retain vial 30 within the syringe body 2.28 as best seen in FIG. 25. An encircling wire clip 2.112, received in circumferential groove 2.114 of shaft 2.35, retains spring 2.104 and sleeve 2.102 on shaft 2.35 when anesthesia vial 30 is not present. After the anesthesia has been administered, plunger 2.36 can be retracted, such that wire clip 2.112 will engage with the narrowed bore 2.116 of sleeve 2.102, thereby retracting sleeve 2.102 against compression spring 2.104 as barb 2.37 disengages from plug 31, thereby allowing the used anesthesia vial 30 to be removed.

Syringe with light combination 2.40 includes an electrical circuit 2.56 integral with syringe and light combination 2.40, including at least one lamp 2.58 and preferably three lamps 2.58. Electrical circuit 2.56 preferably includes a first circuit board 2.57 and a second circuit board 2.59, interconnected by wires 2.61. Mounted to first circuit board 2.57 are one or more batteries 2.70, each within a well-known battery holder 2.74. Preferably at least one of batteries 2.70 completes its circuit through a contacting plated-through hole 2.78 on circuit board 2.57, and an insulating strip 2.118 is interposed between plated-through hole 2.78 and battery 2.70, thereby interrupting the contact to battery 2.70. When circuit board 2.57 is mounted into battery compartment 2.72, plated-through hole 2.78 is exposed and insulating strip 2.118 is left hanging outside the battery compartment 2.72, as best seen in FIG. 18. To test the operation of electrical circuit 2.56, a conducting (metallic) needle is inserted through plated-through hole 2.78 and through insulating strip 2.118 to battery 2.70, thereby completing the circuit between battery 2.70 and plated-through hole 2.78, thereby causing lamps 2.58 to illuminate for testing during manufacture. Removal of the test needle again causes battery 2.70 to be insulated from plated-through hole 2.78 by insulating strip 2.118, and the top 2.73 of battery compartment 2.72 is closed with insulating strip 2.118 extending outside of battery compartment 2.72, again as best seen in FIG. 18.

To illuminate the lamps 2.58 during normal use by a dentist, the dentist simply pulls the insulating strip 2.118 from the battery compartment 2.72 (see dotted lines in FIGS. 19 and 20), thereby permitting plated-through hole 2.78 to contact battery 2.70, thereby completing the circuit and causing the battery to power lamps 2.58. Insulating strip 2.118 is thus seen to function as a single-use switch to turn the lamps on during use.

Second circuit board 2.59 is mounted to distal end 2.46 of body 2.28, and a transparent cap 2.98 covers circuit board 2.59 and lamps 2.58, and lamps 2.58 shine through transparent cap 2.98.

With the exception of spring 2.104, electrical circuit 2.56, and wire clip 2.112, all parts of second embodiment 2.40 are preferably constructed of a sterilizable plastic so that second embodiment 2.40 can be sterilized, enclosed in a sterile package, opened by the dentist and used, and then discarded after use on a single patient, thereby reducing transmission of germs and diseases between patients. The dentist uses the second embodiment to administer anesthetic just as with the first embodiment.

Improvements have been made to the third preferred embodiment light 3.40, hereinafter described, that provide for ease of construction and assembly as compared to the first preferred embodiment, and the third preferred embodiment light 3.40 is disposable so that it can be pre-sterilized and provided in a sealed sterile package that is opened when the syringe is needed to be used, and then the third preferred embodiment light 3.40 can be disposed of after its single use. Additionally, because the third preferred embodiment is used with a well-known oral injection syringe that has already been approved by governmental approval bodies for use in dentistry with patients, regulatory approval is not required for the third preferred embodiment light 3.40 that attaches to the already-approved oral injection syringe. Otherwise, the third embodiment has many similarities to the first and second embodiments.

Light 3.40 includes a barrel 3.42 having a proximal end 3.44 and a distal end 3.46, and barrel 3.42 has a first opening 3.48 at proximal end 3.44 and a second opening 3.50 at distal end 3.46. Barrel 3.42 further has a longitudinal passageway 3.52 therethrough from first opening 3.48 to second opening 3.50, with passageway 3.52 having a transverse inner diameter 3.54 larger than the certain body outer diameter 38, for closely receiving the tubular body 28 of syringe 20 therewithin, with the tubular body 28 of syringe 20 extending through the first opening 3.48 and with the needle 22 extending out of the second opening 3.50 as best seen in FIGS. 26 and 28. Preferably the transverse inner diameter 3.54 is about 1 mm or so larger than the certain body outer diameter 38 so that the syringe 20 will be frictionally retained within the passageway 3.52 of light 3.40. It will be understood that first opening 3.48, second opening 3.50, and passageway 3.52 are preferably co-axial on the longitudinal axis of barrel 3.42.

Light 3.40 further includes an electrical circuit 3.56 including at least one lamp 3.58 and preferably a plurality of lamps 3.58, such as the two light emitting diode ("LED") lamps shown in the preferred embodiments of light 3.40, proximate the distal end 3.46 of barrel 3.42, preferably around second opening 3.50 so as to fully illuminate the needle 22 and the anesthesia injection site in the patient's mouth.

Referring especially to FIG. 33, third embodiment 3.40 of the light includes a battery compartment 3.72 that holds a battery holder 3.73 having metallic left and right battery contacts 3.74 and 3.76. It should be noted that right battery contact 3.76 has a small hole 3.78 therethrough in alignment with a similar small access hole 3.79 through the right wall of battery compartment 3.72. The left battery contact 3.74 has an inwardly-bent triangular flap 3.80 that engages the positive ("+") terminal of the leftmost battery 3.70 when all three batteries 3.70 are inserted into the battery holder 3.73. Similar to the second embodiment, an insulating strip 3.118 is interposed between right battery contact 3.76 and rightmost battery 3.70, thereby interrupting the circuit and preventing batteries 3.70 from supplying power to the lamps 3.58. After light 3.40 has been assembled, proper operation of circuit 3.56 can be tested by inserting a conducting metallic needle through hole 3.78 from the outside of battery compartment 3.72, through insulating strip 3.118, and contacting the rightmost battery 3.70, thereby completing the circuit between rightmost battery 3.70 and contact 3.76 and allowing batteries 3.70 to supply power to the lamps 3.58.

As seen in FIG. 33, wires 3.61 carry the current to and from lamps 3.58 via circuit board 3.59, and wires 3.61 are received into longitudinal grooves 3.63 within barrel 3.42. A snap-in circuit cover 3.71, having a plurality of laterally-extending tabs 3.120 that matingly engage channels 3.122 in barrel 3.42, is provided to produce a sealed unit, with insulating strip 3.118 extending out of the battery compartment. A transparent cap 3.98 is then fitted to distal end 3.46 of barrel 3.42 over circuit board 3.59 and LED lamps 3.58.

To illuminate the lamps 3.58 during normal use by a dentist, the dentist simply pulls the insulating strip 3.118 from the battery compartment 3.72 (see dotted line in FIG. 32), thereby permitting battery contact 3.76 to contact rightmost battery 3.70, thereby completing the circuit and causing the battery to power lamps 3.58. Insulating strip 3.118 is thus seen to function as a single-use switch to turn the lamps on during use.

With the exception of electrical circuit 3.56, all parts of third embodiment 3.40 are preferably constructed of a sterilizable plastic so that third embodiment 3.40 can be sterilized, enclosed in a sterile package, opened by the dentist and used, and then discarded after use on a single patient, thereby reducing transmission of germs and diseases between patients. The dentist uses the third embodiment to administer anesthetic just as with the first and second embodiments.

INDUSTRIAL APPLICABILITY

The light of the present invention has industrial applicability when used with an oral anesthesia injection syringe in that it illuminates the needle and the interior of a patient's mouth during injection of an oral anesthetic. The light is self-contained and unobtrusive and permits "hands free" operation, following the needle as the syringe is moved within the patient's mouth. Disposable single-use embodiments are provided that are pre-sterilized and discarded after use, thereby reducing transmission of germs from one patient to another.

Although the present invention has been described and illustrated with respect to a preferred embodiment and a preferred use therefor, it is not to be so limited since modifications and changes can be made therein which are within the full intended scope of the invention.

We claim:

1. An oral anesthesia injection syringe having a body, said body having a barrel and also having a proximal end and a distal end, said distal end of said syringe being adapted for receipt of a hypodermic needle thereon, said syringe including an electrical circuit integral therewith, said electrical circuit including:
   (a) a plurality of lamps proximate said distal end of said body and encircling said hypodermic needle;
   (b) a battery received into a compartment on said barrel of said body for powering said plurality of lamps; and
   (c) an insulator selectively and removably interposed between a terminal of said battery and said plurality of lamps;

with said plurality of lamps, when said insulator is removed from being interposed between said terminal of said battery and said plurality of lamps so that said plurality of lamps are powered by said battery and when said hypodermic needle is received on said distal end of said syringe, illuminating said hypodermic needle and an injection site of said hypodermic needle.

2. The syringe as recited in claim 1, in which said syringe is pre-sterilized and disposable after use on a single patient.

* * * * *